US00PP36669P3

(12) United States Plant Patent
Olesen et al.

(10) Patent No.: US PP36,669 P3
(45) Date of Patent: May 13, 2025

(54) ***CLEMATIS* PLANT NAMED 'Evipo119'**

(50) Latin Name: *Clematis viticella*
Varietal Denomination: Evipo119

(71) Applicants: Mogens Nyegaard Olesen, Fredensborg (DK); Raymond J. Evison, St. Sampson Vale (GB)

(72) Inventors: Mogens Nyegaard Olesen, Fredensborg (DK); Raymond J. Evison, St. Sampson Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 25 days.

(21) Appl. No.: 18/831,178

(22) Filed: Sep. 5, 2024

(65) Prior Publication Data

US 2025/0107475 P1 Mar. 27, 2025

(30) Foreign Application Priority Data

Sep. 22, 2023 (QZ) ..... 20231970

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt

(57) ABSTRACT

A new *Clematis* plant with a compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo119'.

This application claims priority to Plant Breeder's Rights Application Number 2023/1970, which was filed at the Community Plant Variety Rights Office in the European Union on Sep. 22, 2023, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo119' originated as a single seedling from the stated cross.

The new *Clematis* plant may be distinguished from its female seed parent and male pollen parent by the following characteristics. The female seed parent grows to a height of 1 meter while the new variety is more compact, growing to a height of 30 cm. The male seed parent has lavender tepals while the new variety has white tepals.

The objective of the hybridization of this *Clematis* plant was to create a new and distinct variety for nursery culture with unique qualities such as:

1. Uniform and abundant pure white flowers;
2. Vigorous and compact growth, making the variety suitable for container culture; and 3. Improved disease resistance.

This combination of qualities was lacking in *Clematis* plants that were in commercial cultivation and the qualities have been substantially achieved in the new variety.

'Evipo119' was selected by Mogens N. Olesen and Raymond J. Evison in their *Clematis* development program in the Channel Islands, United Kingdom in 2008. Asexual reproduction of 'Evipo119' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo119' are true to type and are transmitted from one generation to the next.

BRIEF DESCRIPTION OF THE DRAWINGS

The accompanying color illustrations show as true as is reasonably possible to obtain in color photographs of this type the typical characteristics of the buds, flowers, leaves, and stems, of 'Evipo119'.

Specifically illustrated in FIG. 1 of the drawings are open flowers viewed from above and underneath, tepals detached revealing the reproductive flower parts, and a flower bud at various stages of development.

DETAILED DESCRIPTION OF THE VARIETY

Figure 1:
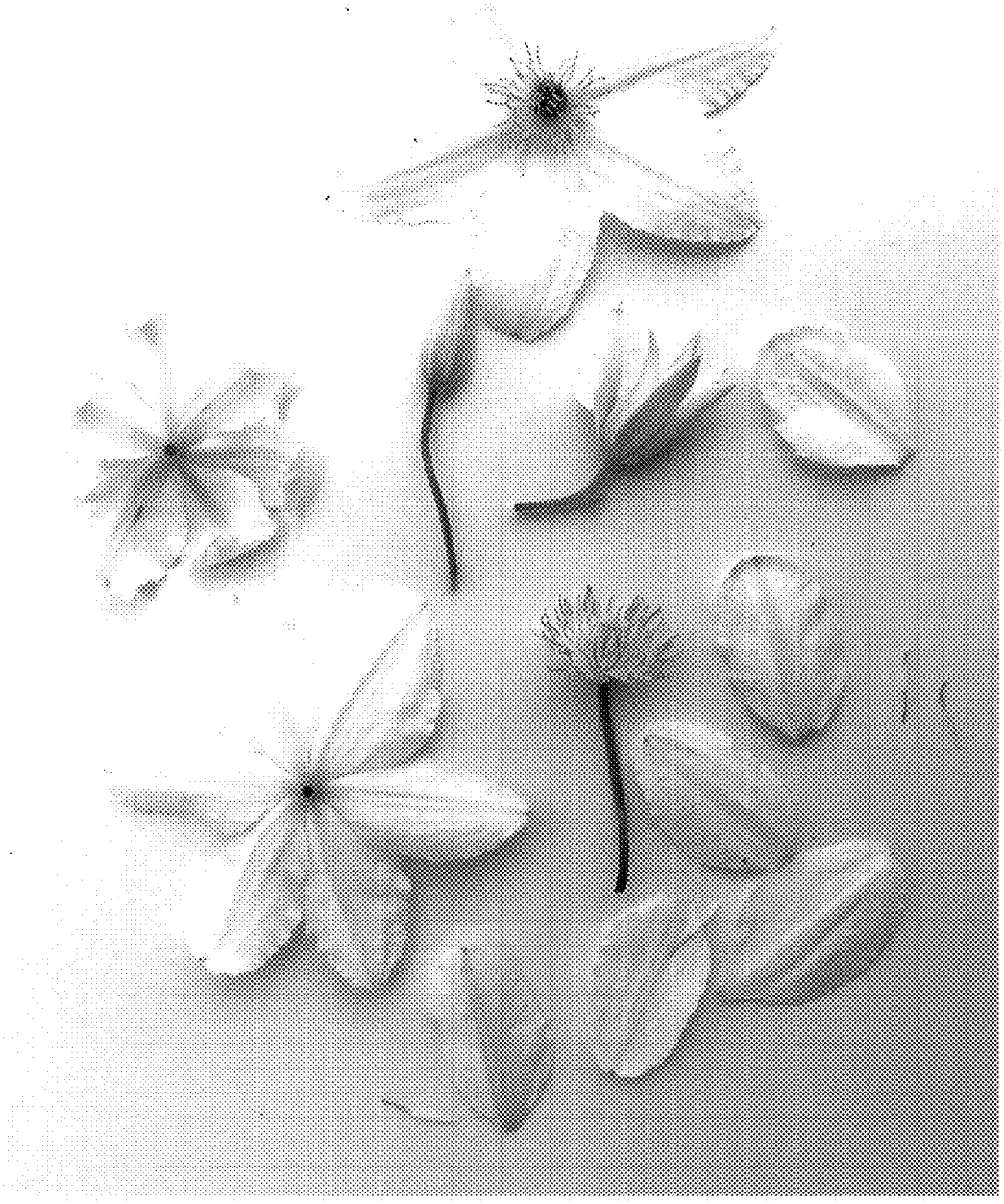
Figure 2:
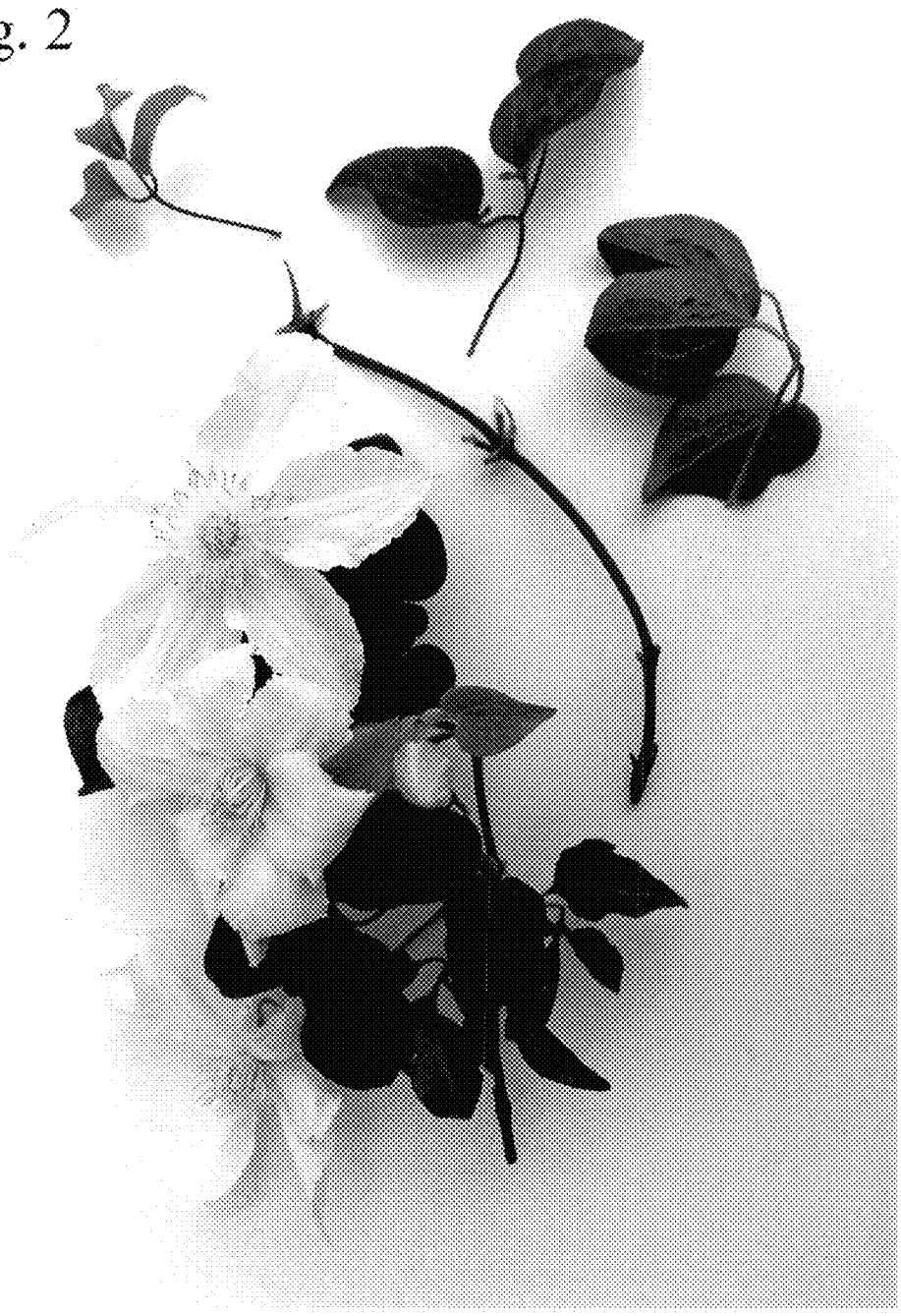
FIG. 2 shows a cluster of flowers on the vine, leaves detached showing the characteristics of the stem. Illustrated plants are 2 years of age.

The following is a detailed description of 'Evipo119', as observed in its growth throughout the flowering period in Odense Denmark. Observed plants were cultivated outdoor for a period of 18 months in 16 cm containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, physical characteristics of the *Clematis* variety 'Evipo052' described and illustrated in U.S. Plant Pat. No. 28,600 are compared to 'Evipo119'. While 'Evipo119' grows to a height of 30 cm, 'Evipo052' grows to a height of 50 cm. Tepal margins of the claimed plant have strong undulations, while those of 'Evipo052' do not have any undulations.

FLOWER AND FLOWER BUD

Blooming habit: Continuous. The natural flowering period is generally from April to September.

Flower bud:
- *Size*.—Normally 31 mm in length. Diameter is 11 to 13 mm.
- *Bud form*.—Long campanulate, broad based.
- *Bud color*.—White Group 155 A with intonations of Yellow-Green Group 145D.
- *Texture*.—Highly pubescent.

Pedicel:
- *Surface texture*.—Smooth.
- *Length*.—25 to 50 mm in length with 3 mm diameter.
- *Color*.—Yellow-Green Group 146C and Yellow-Green Group 145B.
- *Strength*.—Moderate.

Receptacle:
- *Surface texture*.—Pubescent.
- *Shape*.—Broad funnel.
- *Size*.—2 mm (h)×4 mm (w).
- *Color*.—Yellow-Green Group 145D.

Flower arrangement:
- *Location on vine*.—New growth only.
- *Borne*.—Normally in clusters of 5 to 7 flowers per flowering stem. Usually 8 stems produced, resulting in 40 to 56 flowers on the entire plant.

Flower bloom:
- *Size*.—On average, flowers are 11 cm in diameter and 10 mm in depth.
- *Profile*.—Open flowers are flat.
- *Fragrance*.—None.
- *Lasting quality*.—Flowers normally remain up to 10 days on the plant.

Tepals:
- *Tepal color*.—Upon opening, the upper surface is White Group 155B with intonations of Yellow Group 4D appearing as a central bar. The lower surface is White Group 155C with intonations of Yellow-Green Group 150D appearing as a central bar. After opening, the upper surface is White Group 155C. The lower surface is White Group 155C.
- *Quantity*.—Normally 6 tepals.
- *Size*.—50 mm in length by 26 mm wide.
- *Shape*.—Individual tepal shape is obtuse. The tepal apex is rounded with a small point. The tepal base is obtuse.
- *Overlap*.—Partial.
- *Apex recurvature*.—Slightly recurved or none.
- *Tepal cross section*.—Flat.
- *Margins*.—Entire. Strong undulations of margin observed.
- *Texture*.—Somewhat rugose.
- *Persistence*.—Tepals drop off cleanly after 10 days.

Reproductive organs:
- *Pollen*.—None observed.
- *Anthers*.—Size: 5 mm in length. Color: Yellow White Group 158D. Quantity: On average, 60.
- *Filaments*.—Color: White Group 155A. Length: 7 mm.
- *Pistils*.—Quantity: . On average, 20.
- *Stigmas*.—Colour: White Group 155C.
- *Styles*.—Color: Green-White Group 157A Length: 11 mm.

PLANT

Plant form: Climbing yet very compact.

Plant growth: Compact.

Size: Seasons growth attains about 30 cm in height. Average spread is 53 cm.

Stems:
- *Color*.—Juvenile stems are Yellow-Green Group 144A with intonations of Greyed-Orange Group 176A. Mature stems are Greyed-Orange Group 175B.
- *Internodes*.—On average, 3 to 5 cm between nodes.
- *Length*.—Normally 13 cm from the base of the plant to the flowering portion of the stem.
- *Diameter*.—About 3 mm.
- *Texture*.—Mature stems are sharply ribbed. Juvenile stems are pubescent.

Plant foliage:
- *Leaf characteristics*.—Deciduous.
- *Arrangement*.—Trifoliate.
- *Leaf size*.—Compound leaves are about 110 mm (l)×90 mm (w). Leaflets are about 55 mm (l)×38 mm (w).
- *Abundance*.—On average leaves per 10 cm of stem.
- *Leaf color*.—Juvenile upper Yellow-Green Group 146B with intonations of Greyed-Red Group 178A. Juvenile lower Yellow-Green Group 146C. Mature upper Yellow-Green Group 147A to 147B. Mature lower Yellow-Green Group 147B.
- *Stipules*.—Absent.
- *Petioles*.—Size: Normally 35 mm in length by 1 to 2 mm diameter. Texture: Smooth. Color: Yellow-Green Group 144A with anthocyanin Greyed- Red Group 178A.
- *Petioloule*.—Size: About 20 mm in length by 1 mm diameter. Texture: Somewhat rugose. Color: Yellow-Green Group 144A with anthocyanin Greyed- Red Group 178A.
- *Leaflet shape*.—Broad lanceolate. The base is oblique, the apex is. acute.
- *Margin*.—Entire with occasional cleft.
- *Surface*.—The upper side is smooth, the lower side is smooth.
- *Thickness*.—Moderate.
- *Glossiness*.—Slightly glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo119', substantially as described and illustrated herein.

* * * * *